(12) United States Patent
Winkler et al.

(10) Patent No.: US 8,193,001 B2
(45) Date of Patent: Jun. 5, 2012

(54) COMPOSITIONS AND METHODS FOR PRESERVING RNA IN BIOLOGICAL SAMPLES

(75) Inventors: Matthew M. Winkler, Austin, TX (US); Richard C. Conrad, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 12/390,702

(22) Filed: Feb. 23, 2009

(65) Prior Publication Data

US 2009/0197346 A1 Aug. 6, 2009

Related U.S. Application Data

(62) Division of application No. 10/360,784, filed on Feb. 5, 2003, now Pat. No. 7,517,697.

(51) Int. Cl.
*G01N 33/00* (2006.01)

(52) U.S. Cl. ......... 436/174; 436/127; 436/131; 436/132

(58) Field of Classification Search .................. 436/174, 436/127, 131, 132
See application file for complete search history.

(56) References Cited

U.S. PATENT DOCUMENTS

| 5,256,571 | A | 10/1993 | Hurley et al. |
| 6,458,322 | B1 | 10/2002 | Harris |
| 2001/0016312 | A1 | 8/2001 | Lader |

FOREIGN PATENT DOCUMENTS

| EP | 0511430 | | 11/1992 |
| EP | 1044984 | | 10/2000 |
| GB | 2412913 | | 7/2007 |
| WO | WO 00/06780 | | 2/2000 |
| WO | WO 00/08202 | * | 2/2000 |
| WO | WO 2004/027024 | | 4/2004 |

OTHER PUBLICATIONS

Eder et al., "Studies on the extraction of phospholipids from erythrocyte membranes in the rat," *Clin. Chim. Acta*, 219(1-2):93-104, 1993.
Chomczynski, "A reagent for the single-step simultaneous isolation of RNA, DNA, and proteins from cell and tissue samples," *Biotechniques*, 15(3):532-536, 1993.
Esser et al., "Isolation of full-size mRNA from ethanol-fixed cells after cellular immunofluorescence staining and fluorescence-activated cell sorting (FACS)," *Cytometry*, 121(4):382-386, 1995.
Fukatsu, "Acetone preservation: a practival technique for molecular analysis," *Mol. Ecol.*, 8(11):1935-1945, 1999.
Folch et al., "A simple method for the isolation and purification of total lipides from animal tissues," *J. Biol. Chem.*, 226(1):497-509, 1957.
Liedtke et al., "A comparison of methods for RNA extraction for RT-PCR," *PCR Methods and Applications*, 4(3):185-187, 1994.

(Continued)

*Primary Examiner* — Sam P Siefke

(57) ABSTRACT

The present invention concerns methods and compositions to prepare biological samples to preserve the macromolecules in the samples. Embodiments of the invention concern the use of a soak solution that contains one or more water-miscible solvents. A sample is incubated with the soak solution to the point of saturation at a temperature above the melting temperature of the water-miscible solvent but below 0° C. The use of methods and compositions of the invention allow for subsequent preparation or analysis of the samples.

18 Claims, 6 Drawing Sheets

OTHER PUBLICATIONS

Marmer and Maxwell, "Dry column method for the quantitative extraction and simultaneous class separation of lipids from muscle tissue," *Lipids*, 16(5):365-371, 1981.

Mukhopadhyay and Roth, In: *RNA Isolation and Characterization Protocols*, Rapley and Manning Ed., Humana Press, Inc., Totowa, NJ, 55-59, 1998.

Safneck et al., "Fixation techniques for fine needle aspiration biopsy smears prepared off site," *Acta Cytol.*, 45(3):365-371, 2001.

Written Opinion and Search Report mailed Jul. 19, 2006 for PCT/US2004/003012 filed Feb. 3, 2004 entitled "Compositions and Methods for Preserving RNA in Biological Samples;" Inventors: Matthew M. Winkler and Richard C. Conrad; Applicant: Ambion Inc.

* cited by examiner

COMPOSITIONS AND METHODS FOR PRESERVING RNA IN BIOLOGICAL SAMPLES

The present application is a divisional application of, and claims priority to, pending U.S. patent application Ser. No. 10/360,784 filed Feb. 5, 2003, to Winkler et al. Said patent application is incorporated herein in its entirety.

FIELD OF THE INVENTION

The present invention relates generally to the fields of cell biology and molecular biology. More particularly, it concerns methods and compositions to prepare a biological sample, such as a fresh or frozen tissue sample, to enhance the preservation of biological macromolecules in the sample. Methods and compositions of the invention include one or more water-miscible solvents that have a freezing temperature below the freezing temperature of water. Such compositions make frozen tissue samples easier to process for the removal of biological macromolecules while protecting them from degradation.

DESCRIPTION OF RELATED ART

The field of molecular biology has a high demand for RNA samples extracted from isolated animal and plant tissues, as well as cultured cells. These samples are analyzed to ascertain changes in the steady-state expression levels of mRNAs in response to disease or experimental stress between different samples. The analysis is performed by a variety of methods, including reverse-transcription polymerase chain reaction (RT-PCR®), Northern blot hybridization, nuclease protection assays, and, more recently, gene array analysis.

For studies of the purified RNA samples to be meaningful, they must accurately reflect the RNA population in the cells at the time of isolation. This means that immediately after the sample is obtained, measures should be taken so that no RNA is created or destroyed in the interval from sample collection to RNA purification. From both a theoretical and practical viewpoint, the degradation of RNA is the more problematic process, as synthesis is a delicately balanced process that tends to become disrupted with the shift in metabolism that occurs with tissue excision. The removal of energy sources that occurs with sample collection shifts the balance to primarily catabolic processes, which results in the inappropriate degradation of RNA by components normally meant to remove older or inappropriate RNA molecules. The process of tissue collection (presumably by excising it from its source) represents the first of several stages where degradation of RNA may occur.

After a sample is collected, it is conveyed to an appropriate homogenization medium, which contains denaturants (e.g., guanidinium salts, reductants, and detergents) that inactivate RNA degradation enzymes and disrupt complexes on contact to release RNA into solution. Once in this medium, the tissue usually has to be mechanically disrupted to break up insoluble tissue components and allow full penetration of the denaturants in which it is homogenized. The final isolation of RNA from this homogenate usually entails an actual chemical extraction of RNA from its cellular milieu such as: absorption of the RNA to a solid support, precipitation of the RNA from the denaturation solution, or extraction of the protein component of the mixture using organic solvents such as phenol and chloroform. A great deal of work has been done to assemble homogenization solutions that work quickly upon tissue disruption and do not allow any biochemical processes to occur during the extraction that might alter mRNA and protein levels. However, these do not address the other stages at which degradation may occur; specifically the time required to convey the tissue sample to homogenization solution and the time in this solution prior to physical disruption of the tissue.

In some cases the sample isolation must be performed away from a laboratory setting, and the delay between sample collection and RNA isolation is quite extended. Alternatively, sometimes it is not desirable to immediately process the tissue and extract RNA. In these instances, the preferred method for stopping cellular metabolism is by quick-freezing the tissue samples, usually by immersion in liquid nitrogen. The downstream processing required to extract the RNA from samples frozen in this manner can be quite laborious.

It is well known that for intact RNA to be obtained from frozen tissue samples, it must be extracted with a minimum of thawing taking place (see Rapley and Manning, 1998). It is thought that ice damages the normal barriers formed between cellular compartments, so that nucelolytic enzymes in degradosomes, cytoplasmic vesicles, and extracellular regions are allowed ectopic access to cytoplasmic and nuclear RNA. To minimize this effect, the preferred method to process frozen tissue is to grind it to a fine powder while maintaining its frozen state, using a specialized refrigerated pulverizing machine or a mortar and pestle kept constantly frozen with dry ice or liquid nitrogen. Since few researchers have access to refrigerated pulverizers, the latter process is routinely used. This is time- and labor-intensive, requiring pre-chilling the mortar and pestle slowly in a $-80°$ C. freezer (plunging in liquid nitrogen tends to crack the ceramic), donning insulated gloves to handle the chilled pestle, and continuously adding liquid nitrogen to the mortar during the process of grinding. The grinding process is laborious, often taking 5 minutes for a one grain sample. If several samples need to be processed in this fashion, a separate mortar and pestle must be used for each, or the apparatus must be thawed, thoroughly cleaned, and re-chilled prior to the next use.

Once pulverized, the powder can then be poured from the frozen mortar into a chilled container for further storage or directly into cold homogenization solution and immediately homogenized to ensure rapid penetration of protein denaturants and inactivation of endogenous nuclease activity. Once in the denaturation solution, the sample can be further homogenized by mechanical blenders, rotor-stator homogenizers, or shear-type homogenizers which pass the solution through a thin space between a plunger and reinforced test tube several times, often while mechanically rotating the plunger. Transfer to the homogenization vessel can be problematic. Since the ambient air is substantially warmer than the sample (even if the procedure is performed in a cold room), atmospheric moisture tends to condense on the sample, causing the powder to clump and stick to the side of receiving vessels, creating masses of tissue thawing out before being homogenized or even submerged in the homogenization solution.

As an alternative, some researchers will grind tissue with frozen homogenization solution, then thaw the powder after the tissue and homogenization solution are thoroughly ground and blended together. With any of these homogenization procedures, a finite amount of time is required to process the sample to uniformity, and during this time, there is the potential for degradation. Thus, with current techniques, there is the dual problem of thawing on transfer or in homogenization solution and the laborious process of grinding tissue at $-80°$ C. or lower (liquid nitrogen boils at $-195.8°$ C.).

The prevalent use of cryostorage for archiving tissues makes any method for the alleviation of the chore of pulverizing into powder before the actual extraction of RNA extremely desirable.

There is currently no procedure or product specified to maintain the intactness of the RNA in a frozen sample while transitioning the sample to a non-brittle state. The term 'frozen' refers to a state where the water contained in the tissue sample is physically present in a solid state. Obviously frozen tissue is a solid mass, and therefore extremely recalcitrant to having solutions diffuse into it. Although tissues can be saturated with preservative solutions at warmer temperatures (e.g., RNAlater™, Ambion, Inc., Austin Tex.), aqueous solutions will be solid at the temperature used to store frozen samples (usually −80° C. or colder). There are reports that solutions of ethanol (U.S. Pat. No. 5,256,571; Safneck et al., 2001, Esser et al., 1995) and acetone (Fukatsu, 1999) provide limited protection for RNA when used to saturate tissues above 0° C. (usually 4° C. or room temperature), although, these are not widely used.

Thus, there is a need for improved methods and compositions that render frozen biological samples tractable for immediate homogenization, as well as for methods and compositions that preserve as many macromolecules from the sample as possible. A method enabling the use of tissue pieces instead of powdered tissue would greatly simplify handling and processing.

SUMMARY OF THE INVENTION

The present invention provides methods and compositions for converting a biological sample into a state that allows for its further manipulation while maintaining the integrity of the sample's macromolecules. For example, frozen tissue may be converted to a softer form while maintaining sub-zero temperatures, allowing the macromolecules within to maintain their intactness so that the converted sample can be employed in future analysis. Future analysis may involve transferring the sample to homogenization solution without the need for constant refrigeration, allowing the sample to be readily processed by commonly-used homogenization systems. Alternatively, the sample may subsequently be prepared for histological analysis, such as by slicing it and placing it on a slide for further observation.

Biological samples of the invention are understood to refer to any sample from an organism. They are contemplated to be or to include cells, tissues, organs, and/or organisms, though it is specifically contemplated that some of these may not be included as part of some embodiments of the invention. Biological samples may be obtained from any organism, including prokaryotes and eukaryotes. Biological samples from mammals, particularly humans, are specifically contemplated by the invention. Biological samples may be obtained by any method, such as dissection, resection, blood sample, other bodily fluid sample, aspiration, lavage, swabbing, rinse, or biopsy. Samples may or may not be frozen prior to implementation of methods of the invention. In some cases, samples are flash frozen, such as with liquid nitrogen, before being subjected to methods and compositions of the invention. The term "macromolecule" refers to large complex organic molecules and is understood to include proteins, nucleic acids (DNA or RNA), carbohydrates, and lipids.

The invention specifically includes methods for preparing a biological sample. In some embodiments, methods involve saturating a biological sample in a "soak" solution that is at least 50% comprised of one or more water-miscible solvents having a melting temperature below 0° C., wherein the saturating occurs at a temperature below 0° C., but above the melting temperature of any water-miscible solvent. The "soak" solution will replace the solid frozen water in the tissue converting it from a solid difficult to homogenize block to a rubbery or leathery tissue that can be more easily cut into smaller pieces and homogenized.

The invention covers the use of a "soak" solution of which at least 50% of it, by volume, is made up of a water-miscible solvent or water-miscible solvents. In other words, a single water-miscible solvent makes up at least 50% of the solution (v/v) or a combination of water-miscible solvents, make up at least 50% of the solution (v/v). It is contemplated that the solution is or is at least 10, 15, 20, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84; 85, 86, 87, 88, 89, 90, 91, 92, 93, 94, 95, 96, 97, 98, 99, or 100% comprised of one or more water-miscible solvents having a melting temperature below 0° C. Alternatively, the soak solution is 25% to 100%, 50% to 90%, or 60% to 80% comprised of one or more water-miscible solvents having a melting temperature below 0° C. In further embodiments of the invention, the pH of the soak solution may be in the range of about 1-10, 3-9, 4-8, or 5-6. The pH of the soak solution may be adjusted to reach such levels. Adjustments may be accomplished using a variety of solutions, including the use of glacial acetic acid for example.

A "water-miscible solvent" refers to a liquid substance that is capable of being dissolved in liquid water in any proportion. A water-miscible solvent refers to a solvent that is fully miscible in water, such that there is no observable phase when the liquids are mixed. In limited embodiments of the invention a "partial water-miscible solvent" may be employed. The water-miscible solvents that having a melting temperature below 0° C., may have a melting temperature below −5, −10, −15, −20, −25, −30, −35, −40, −45, −50, −55, −60, −65, −70, −75, −80, 85, −90, −95, −100° C. or even lower.

Water-miscible solvents of the invention include, but are not limited to, alcohols. Alcohols that can be used are described throughout this specification, including ethanol, 1-propanol, methanol, isopropaniol, methoxyethanol, alkyl alcohol, nitroethanol, or a combination thereof. Other water-miscible solvents that can be included in the soak solution are ethyl acetate, ethylainine, acetone, 2-aminopropane, acetaldehyde, or diethylene glycol monoethyl ether.

It is specifically contemplated that solutions and compositions of the invention contain at least one water-miscible solvents having a melting temperature below 0° C., and in some embodiment, they are comprised of or comprised at least of 1, 2, 3, 4, 5, 6, 7, 8, 9, 10, or more such water-miscible solvents.

Other additives may be included in the soak solution such as those that help maintain the integrity of macromolecules or facilitate their isolation. Such additives could be emulsifying agents, such as detergents, and/or inhibitors targeting agents that compromise the integrity of the macromolecule(s) of interest (referred to as "inhibiting agents"). Inhibiting agents in methods and compositions of the invention may function covalently or noncovalently to effect inhibition of agents that damage macromolecules. For example, the agents could be protein modification agents that act against proteases, RNases, DNases, or other inhibitors that reduce the activity of these enzymes. In some embodiments of the invention, the protein modification agent is an acetylating agent, a halogenating agent, nucleotides, nucleic acid analogs, amino acids, amino acid analogs, or carbodiimides and imides. Covalent inhibiting agents of the invention include, but are not limited to, haloacetates, haloacetamides, acetylsalicyclic acid, and acid anhydrides. When such inhibitors agents are employed in solutions of the invention, the pH of the soak solution may be adjusted to between 4 to 8 or between 5 to 6. It also may be at about 1, 2, 3, 4, 5, 6, 7, 8, 9, 10. In specific embodiments of the invention the inhibiting agent is a DNase or RNase inhibitor. The solution may have other low molecular weight inhibitors of enzymes which degrade RNA, DNA or protein.

It is contemplated that the soak solution may have none of the additives described in the previous paragraph, or it may have or have at least 1, 2, 3, 4, 5, 6, 7, 8, 9, 10 or more such additives. The soak solution may have DMSO in it. In some embodiments of the invention, the soak solution is comprised or comprised up to 1, 2, 3, 4, 5, 6, 7, 8, 9 10, 11, 12, 13, 14, 15, 16, 17, 18, 19, 20% or more DMSO (v/v).

In some embodiments of the invention, there is or is at least 1, 2, 3, 4, 5 or more inhibiting agents. The total amount of the inhibiting agents in the soak solution may be or may be up to 1, 2, 3, 4, 5, 6, 7, 8, 9 10, 11, 12, 13, 14, 15, 16, 17, 18, 19, 20% or more (w/v or v/v). Such inhibiting agents may be employed with or without DMSO. Alternatively, in some embodiments of the invention, the soak solution has DMSO but does not have any inhibiting agents. In specific embodiments, the inhibiting agent is an RNase inhibitor, which may be with or without DMSO in the soak solution. In other embodiments, the inhibiting agent is a protein modification agent. Soak solutions may have an RNase inhibitor(s) and/or a protein modification agent(s) at a concentration of or of at least 1, 2, 3, 4, 5, 6, 7, 8, 9 10, 11, 12, 13, 14, 15, 16, 17, 18, 19, 20% or more (v/v). In some cases, the soak solution has a protein modification agent, DMSO, and/or an RNase inhibitor. Inhibiting agents may also be in the soak solution at a concentration of or at a concentration of at least 0.01, 0.1, 1, 2, 3, 4, 5, 6, 7, 8, 9 10, 11, 12, 13, 14, 15, 16, 17, 18, 19, 20, 25, 30, 35, 40, 45, 50, 55, 60, 65, 70, 75, 80, 85, 90, 95, 100 U/µl or U/ml.

In some embodiments, it is contemplated that a soak solution is comprised of up to 5% DMSO (v/v), and/or up to 5% protein modification agent (v/v), and the remainder of the solution is a water-miscible solvent having a melting temperature below 0° C.

In additional methods of the invention, the biological sample is in the soak solution (and once saturated may remain in the solution) for or up to 1, 2, 3, 4, 5, 6, 7, 8, 9, 10, 11, 12, 13, 14, 15, 16, 17, 18, 19, 20, 21, 22, 23, 24 or more hours, 1, 2, 3, 4, 5, 6, 7 or more days, 1, 2, 3, 4, 5 or more weeks, 1, 2, 3, 4, 5, 6, 7, 8, 9, 10, 11, 12 or more months, or 1, 2, 3, 4, 5 or more years. In some embodiments, the biological samples is placed in soak solution for up to 3 months, up to 1 week, or up to 48 hours or longer. Alternatively, the biological sample is in the soak solution for 6 to 36 hours or for 16 to 24 hours.

Additional steps of method claims of the invention include homogemizing the biological sample with a homogenization solution after it has soaked and is saturated. A homogenization solution is a solution that aids tissue disruption by dissolving cell membranes as well as denaturing and diluting proteins, thereby rendering them inactive and dissociating all non-covalent complexes between proteins and other proteins or other macromolecules. In some embodiments, the homogenization solution includes one or more protein denaturant, such as a guanidinium salt (for example, guanidinium isothiocyanate), reductants, and/or detergents. Detergents may be ionic or nonionic. Examples of nonionic, nondenaturing detergents that may be included as part of the invention, but should not limit it, are digitonin, NP40, CHAPS, or deoxycholate. Techniques to homogenize a biological sample to preserve macromolecules within the sample are well known to those of ordinary skill in the art and may be employed as part of methods of the invention.

Another step in methods of the invention is extracting a macromolecule from the biological sample after it has become saturated with the soak solution. In some embodiments, nucleic acids are extracted from the sample. It is specifically contemplated that DNA, RNA, or both are extracted from the sample. In other embodiments of the invention, proteins are extracted from the sample. In additional embodiments, carbohydrates and/or lipids are extracted from the sample. It is also specifically contemplated that any combination of macromolecules can be extracted from the sample according to methods of the invention.

Other steps of the invention include preparing a sample for histological analysis. In some embodiments, subsequent to being saturated in a soak solution, a sample may be placed in an isotonic solution such as a sucrose solution. In other embodiments, tissue is sectioned (or cryosectioned) and mounted on a slide. The sample is transitioned to PBS or a sucrose isotonic (solution) before cryosectioning. Alternatively, after the biological sample is saturated in the soaking solution, it may be transitioned directly to xylene and then, paraffin using standard embedding techniques, then cryosectioned for further analysis.

Methods of the invention include a method for preparing a biological sample comprising: saturating the biological sample in a soak solution that is at least 50% comprised of one or more water-miscible solvents having a melting temperature below about 0° C., wherein the "soak" occurs at a temperature below 0° C., but above the melting temperature of any water-miscible solvent; and, extracting a macromolecule from the biological sample.

The present invention also concerns methods for extracting nucleic acids from a biological sample comprising: saturating the biological sample in a soak solution that is at least 50% comprised of one or more water-miscible solvents having a melting temperature below about 0° C., wherein the saturating occurs at a temperature below 0° C., but above the melting temperature of any water-miscible solvent; homogenizing the sample with a homogenization solution comprising a protein denaturant as described above; and, extracting nucleic acids from the sample after the sample is homogenized.

Any of the embodiments discussed above can be employed with these methods of the invention. Similarly, any of the kits discussed below may contain components or reagents discussed above to allow macromolecules to be isolated or extracted from a biological sample.

The invention includes kits for extracting a macromolecule from a biological sample comprising, in a suitable container: a soak solution that is at least 50% comprised of one or more water-miscible solvents having a melting temperature below about −20° C., or i) at least 50% comprised of one or more water-miscible solvents having a melting temperature below about −20° C. and ii) at least 1% comprised of DMSO. Other kits of the invention are kits for extracting a macromolecule from a biological sample comprising, in a suitable container: "soak" solution that is i) at least about 90% ethanol and ii) about 4%-5% comprised of DMSO. In some kits, compositions, and methods of the invention, the "soak" solution is about 94%-95% ethanol and has a pH of about 5. In others, the "soak" solution is about 89%-90% ethanol and 4%-5% of a combination of methanol and isopropanol.

It will be understood that any value in the context of a measurement or quantitation is intended to indicate the inclusion of the standard error for that measurement.

It is specifically contemplated that any embodiments discussed with respect to one aspect of the invention may be applied to other aspects of the invention, and vice versa.

The use of the word "saturate" or inflection thereof, for example "saturating" may mean to permeate, infuse, imbue, impregnate thoroughly, soak, fill, fill completely, load to capacity, drench, wet, sodden, pervade, suffuse, transfuse, douse, souse, to cause to absorb or hold as much of another substance as is possible, or to cause to become completely penetrated (See Roget's II: The New Thesaurus, Third Edition, 1995. Cambridge International Dictionary of English, Merriamn Webster's Collegiate® Dictionary, 10th Edition. Oxford Paperback Dictionary and Thesaurus. The American Heritage® Dictionary of the English Language. Webster's II New Riverside University Dictionary, 1995. Webster's New Twentieth Century Dictionary, $2^{nd}$ Edition, 1983).

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the alt from this detailed description.

BRIEF DESCRIPTION OF THE DRAWINGS

The following drawings form part of the present specification, and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figures 1, 1A:
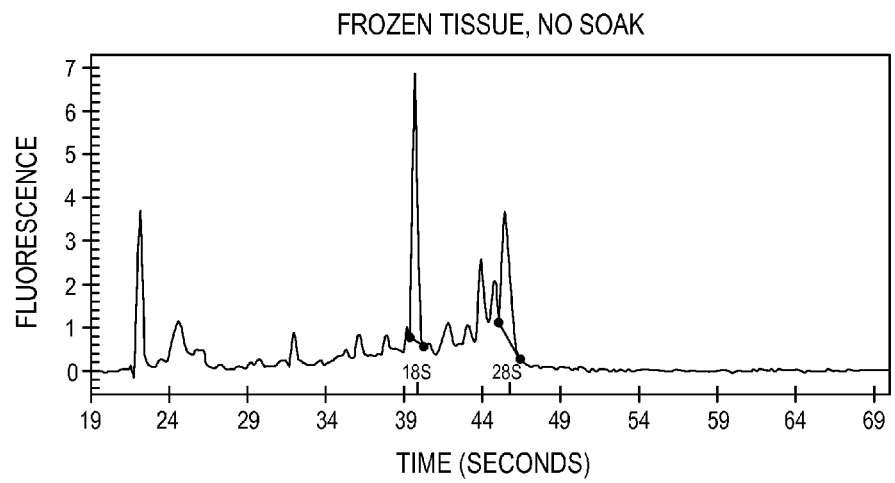
FIG. 1A-1-FIG. 1A-4, FIG. 1B-1-FIG. 1B-4. Capillary electrophoresis scans of RNA extracted from the mouse tissue soaked in the seven organic solvents identified in the figures at −20° C. versus a sample kept frozen and extracted in parallel.
Figures 1, 1A, 2:
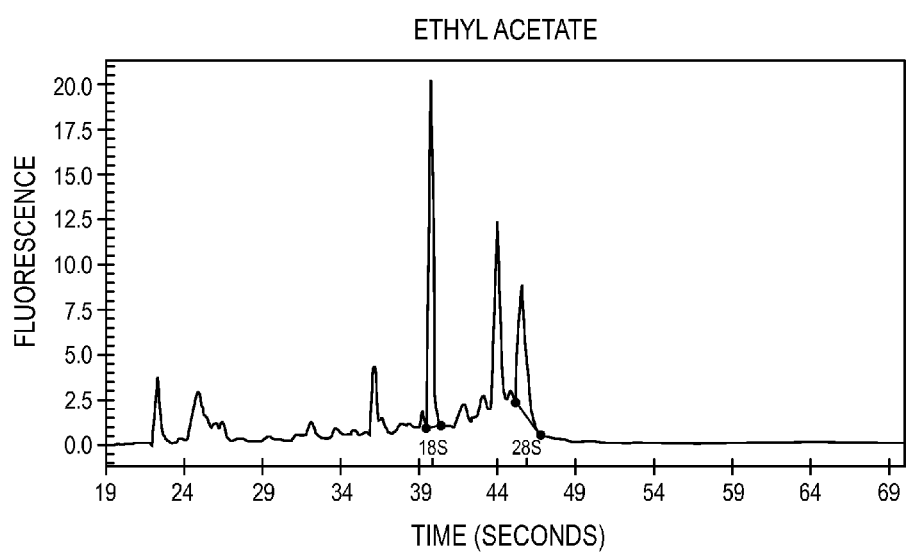
Figures 1, 1A, 2, 3:
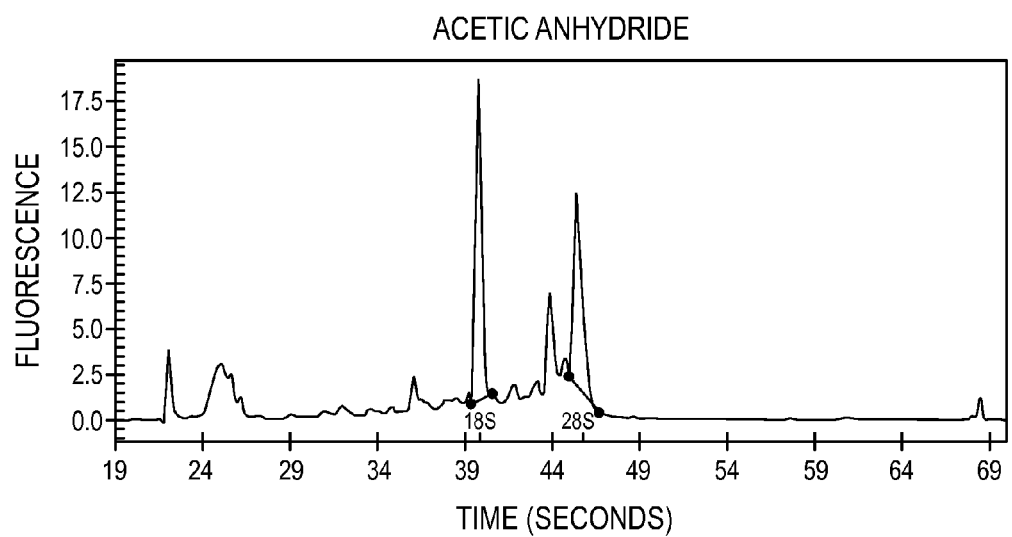
Figures 1, 1A, 2, 3, 4:
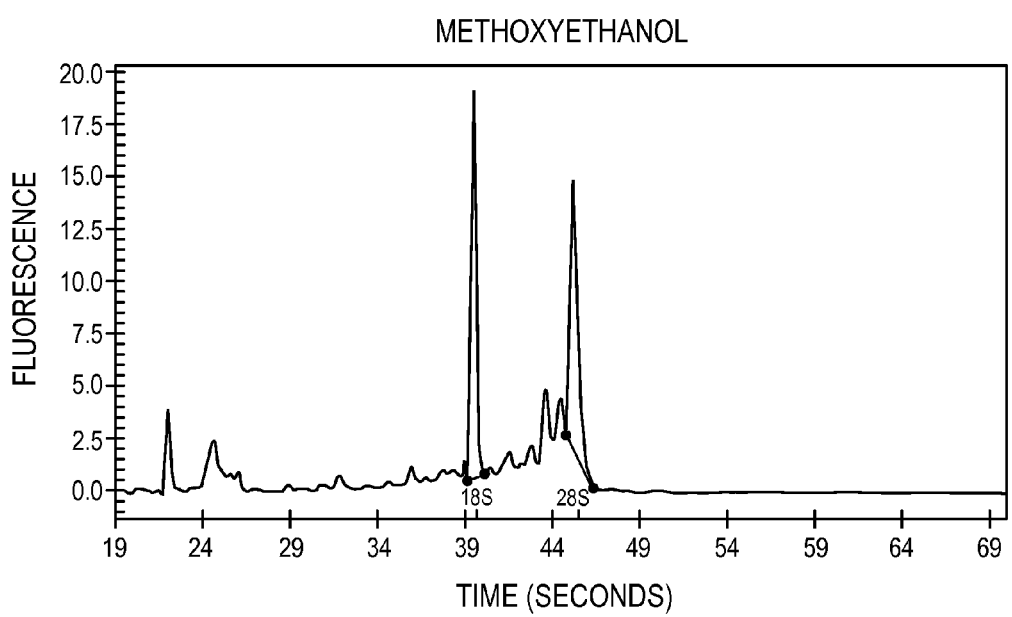
Figures 1, 1B:
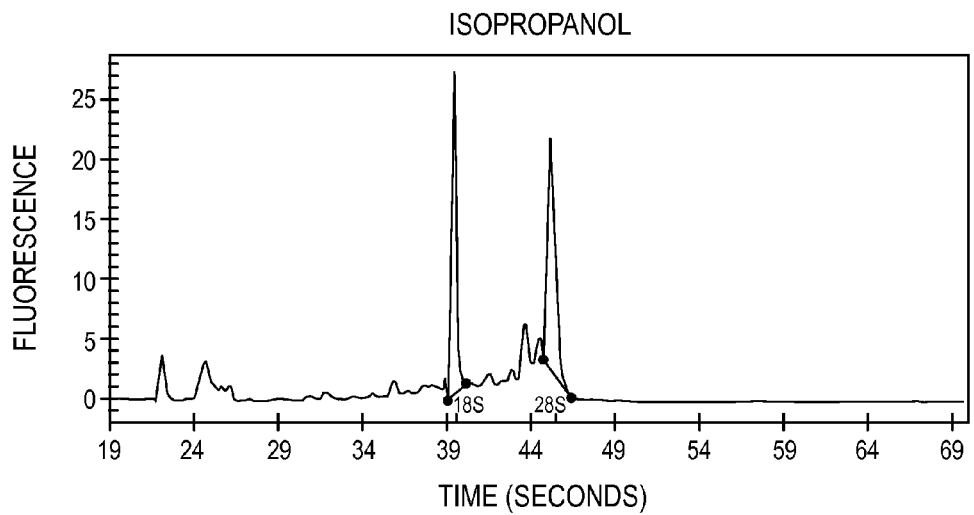
Figures 1, 1B, 2:
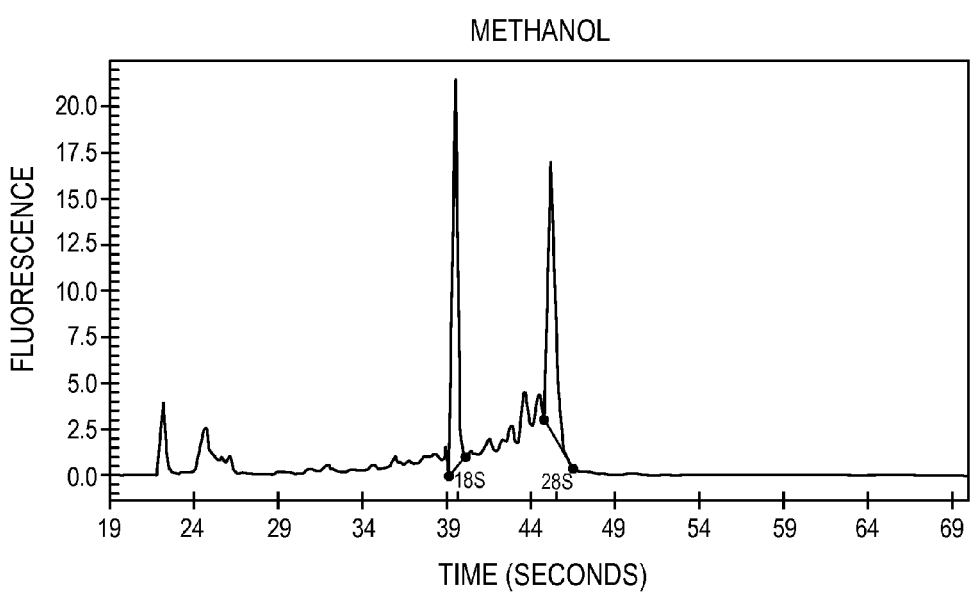
Figures 1, 1B, 2, 3:
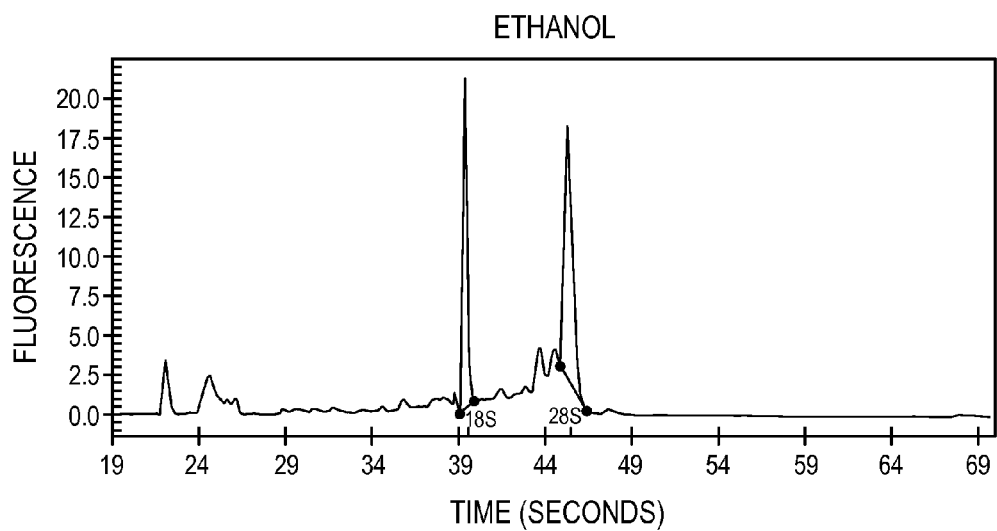
Figures 1, 1B, 2, 3, 4:
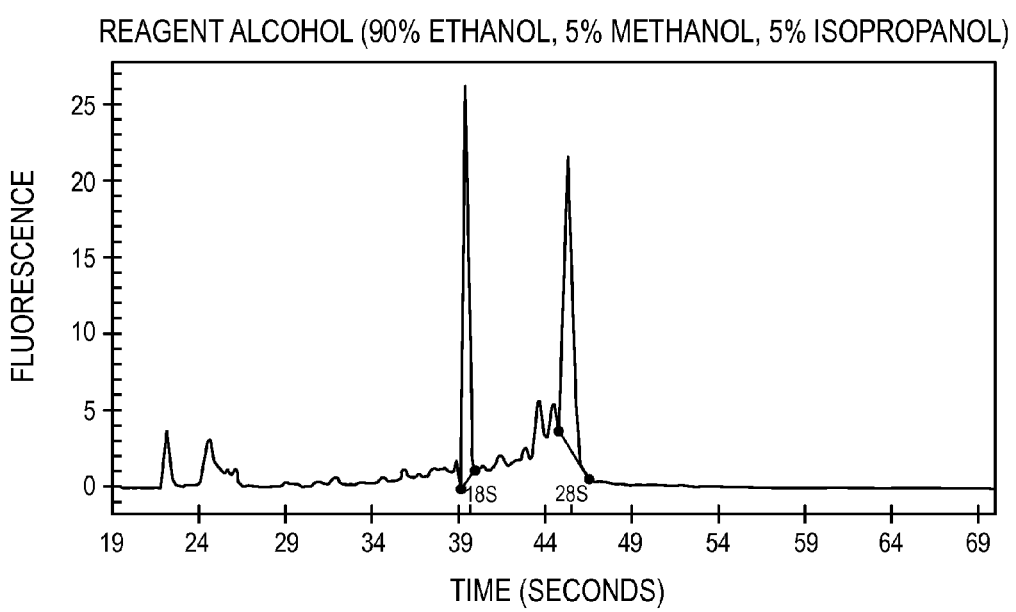

This invention relates to methods and compositions for converting tissue, especially frozen tissue, to a state that can be readily processed by common homogenization methodologies to extract high-quality RNA. In one aspect of the invention, the method uses a relatively anhydrous, but water-miscible solution, with a penetrating agent, to enable the solvent to replace water in the tissue at a rapid rate. In other embodiments, additional agents are included that can lead to more permanent inactivation of the protein contained within the tissue. Tissue thus converted contains RNA that is stable for short periods of time (<60 min) at ambient temperature.

The water-miscibility would enable such solvent to dissolve the solid water, and the low-melting point, would enable the tissue to be maintained at extremely cold temperature (during storage in standard laboratory freezers, primarily −20° C. and −70° C. to −80° C.) during the transfer-to-solvent soak procedure. Nucleases present in the tissue are inactive at first due to the crystalline solid state of the water present, and later to the low temperature and different properties of the solvent relative to water. When the tissue is homogenized, it can be processed by any normal means, as its physical state will no longer be that of a brittle solid, even at very low temperatures, and the water-based lysis buffers (usually with guanidinium thiocyanate and/or detergents) will easily replace the solvent contained in the tissue itself. Because the denaturation agents in the lysis solution will enter coincidentally with the water, the enzymes should not be reactivated, so no interference should occur at this level either.

One way to aid the penetration of these solvents into lipids would be to include an agent that will enable the alcohol to penetrate fatty compounds, such as dimethylsulfoxide (DMSO). An agent such as this may also enhance the penetration of the main solvent and assist in permeabilizing the tissue so that other small molecules can penetrate into the tissue sample as it is rendered malleable. These other small molecules could be specific inhibitors of RNase activity, either covalent or non-covalent, or protein modification reagents that could modify a wide range of proteins, inactivating RNase activity coincidentally.

The following provides additional details about the methods and compositions of the invention. The practice of the present invention will employ, unless otherwise indicated, conventional techniques of biochemistry, cell biology, chemistry, and molecular biology, which are within those of skill in the art. (See, e.g., Sambrook et al., 2001; Ausubel et al., 1994; Harlow And Lane, 1988).

A. Water-Miscible Solvents

The present invention concerns water-miscible solvents. "Miscibility" refers to the "tendency or capacity of two or more liquids to form a uniform blend, that is, to dissolve in each other." It is understood by those of ordinary skill in the art that the term water-miscible solvent in the context of the present invention is synonymous with a "water-miscible solvent."

In some embodiments of the invention, an alcohol qualifies as the water miscible solvent, so long as its melting temperature is below about 0° C. In some embodiments, alcohols of the invention have a melting temperature below about −20° C., below about −70° C., or below about −100° C. Such alcohols may include alkyl alcohols having one to five carbons, such as methanol, ethanol, n-propanol, isopropanol; amides, such as dimethylformamide and dimethylacetamide; cyclic amines, such as 4-piperidine ethanol, N-methyl-4-piperidinol, 2-pyrrolidinone, 1-methyl-2-pyrrolidinone (sometimes referred to as NMP), 5-methyl-2-pyrrolidinone, ethyl pyrrolidinone, propyl pyrrolidinone, 3-pyrrolidinol; ketones and ketoalcohols, such as acetone, and diacetone alcohol; ethers, such as tetrahydrofuran, and soluble glycol ethers; and any of these in any combination.

Ethylene glycol, diethylene glycol oxyethylene or oxypropylene addition dimers, trimers, or polymers, such Was diethylene glycol, triethylene glycol, tetraethylene glycol, dipropylene glycol, tripropylene glycol, polyethylene glycol, or polypropylene glycol; alkylene glycols having an alkylene group of 2 to 6 carbons, such as ethylene glycol, propylene glycol, trimethylene glycol, butylene glycol, 1,2,6-hexantriol, or hexylene glycol; thiodiglycol; glycerin; lower alkyl ethers of a polyhydric alcohol, such as ethylene glycol monomethyl (or monoethyl)ether, diethylene glycol monomethyl (or monoethyl)ether, triethylene glycol monomethyl (or monoethyl)ether, propylene glycol monomethyl (or monoethyl)ether, dipropylene glycol monomethyl (or monoethyl) ether, or tripropylene glycol monomethyl (or monoethyl) ether; lower dialkyl ethers of a polyhydric alcohol, such as triethylene glycol dimethyl (or diethyl)ether, or tetraethylene glycol dimethyl (or diethyl)ether; sulfolane; 1,3-dimethyl-2-imidazolidinone; and any of these in any combination, may permissibly be included in the present invention.

Additional examples of the water miscible solvents include cyclic esters (also referred to as lactones). One example of a suitable water-miscible lactone that may be suitable for use as part or all of the water-miscible solvent is butyrolactone, which is also commonly referred to as BLO, γ-butyrolactone, butyryl lactone, 4-butanolide, 1,4-butanolide, and 1,2-butanolide. The water-miscible lactone(s) may be used in any combination with each other and may also be used in any combination with any of the compounds described in the previous paragraph to form the water-miscible organic solvent.

B. Additives

Other additives may be included in soaking compositions of the invention to facilitate the preservation of a biological sample or extraction of macromolecules.

Agents to enable the alcohol to penetrate fatty compounds. An example is dimethylsulfoxide (DMSO). An agent such as this also enhances the penetration of the main solvent and assists in permeabilizing the tissue so that other small molecules can penetrate into the tissue sample as it is rendered malleable.

These other small compounds could be specific agents targeting enzymes that act to compromise the integrity of the macromolecule(s) of interest, specifically hydrolytic enzymes. For example, the agents could be directed to proteases, RNases, DNases, or other inhibitors that destroy or render nonfunctional, covalently or noncovalently, a particular macromolecule.

It is contemplated as part of the invention, that the following types of agents could be used in compositions or methods described herein: alkylating, acetylating agents, halogenating agents, nucleotides, nucleic acid analogs, amino acids, amino acid analogs, transition state analogs, or reducing agents. The present invention includes, but is not limited to the following covalent inhibiting agents: haloacetates, haloacetamides, acetylsalicyclic acid, and acid anhydrides.

In addition, reagents are commonly available to inhibit proteases and nucleases, such as ANTI-RNase (Ambion), RNAsecure™ (Ambion); or DEPC.

Other additives that may be used with the methods of the present invention include reducing agents and protease inhibitors, which are well known to those of skill in the art. Reducing agents include, for example, 2-mercaptoethanol, dithiothreitol (DTT), pterin, hydrogen sulfide, ascorbic acid, NADPH, tricarboxyethyl phosphine (TCEP), and hexamethylphosphorous triamide (Me2N)3P. An example of an oxidizing agent is 5,5'-dithio-bis(2-nitrobenzoic acid) (DTNB). PMSF is an example of a protease inhibitor.

C. Homogenization of Samples

It is contemplated that the present invention can be used to facilitate preparation of biological samples for evaluation and subsequent use. In some embodiments of the invention, preparation of samples involves homogenizing the sample or preparing a cell lysate from the sample. Typically, homogenization is accomplished using a solution that contains a guanidinium salt, detergent, surfactant, or other denaturant.

Guanidinium salts are well known to those of skill in the art and include guanidinium hydrochloride and guanidinium isothiocyanate. In some embodiments, they may be present in a concentration of about 2 to about 5 M. Additionally, a homogenization solution may contain urea.

A biological sample may be homogenized or fractionated in the presence of a detergent or surfactant. The detergent, particularly a mild one that is nondenaturing, can act to solubilize the sample. Detergents may be ionic or nonionic. Examples of nonionic detergents include triton, such as the Triton X series (Triton X-100, Triton X-100R, Triton X-114, Triton X-450, Triton X-450R), octyl glucoside, polyoxyethylene(9)dodecyl ether, digitonin, IGEPAL CA630, n-octyl-beta-D-glucopyranoside (betaOG), n-dodecyl-beta, C12EO7, Tween 20, Tween 80, polidocanol, n-dodecyl beta-D-maltoside (DDM), NP-40, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), and cetyltrimhethylaminoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Homogenization solutions may further contain other agents such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

In some embodiments of the invention, a homogenization solution includes: 4 M guanidinium thiocyanate, 25 mM sodium citrate, pH 7.2, 0.5% N-lauroyl sarcosine, and 100 mM β-mercaptoethanol. Once the sample has been homogenized into this solution, the RNA can be extracted, often with phenol solutions or the use of an adsorptive solid phase. Alternative methods use combination denaturant/phenol solutions to perform the initial homogenization, precluding the need for a secondary extraction. Examples of these reagents would be TriZol™ (Invitrogen) or RNAwiz™ (Ambion, Inc.)

Subsequent to exposure to a homogenization solution, samples may be further homogenized by mechanical means. Mechanical blenders, rotor-stator homogenizers, or shear-type homogenizers may be employed.

Alternatively, the tissue could be homogenized in the "soak" solution, and the tissue remains separated by settling, centrifugation, or filtration. These remains could then be treated with homogenization solution and extraction conditions as described above.

The methods of the invention may further include steps involving removing lipids or compositions thereof with detergents or surfactants. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof. Removal of a lipid such as a phospholipid is described herein.

D. Extraction/Isolation/Purification of Macromolecules

It is an object of the invention to prepare biological samples to enable their future manipulation. In some aspects of the invention, the future manipulation of the sample is to obtain particular macromolecules from the sample. This can be accomplished by extracting or isolating the macromolecules from the sample. Because of the biochemistry involved in isolating macromolecules from the sample, the terms "extracting" and "isolating" are used synonymously to refer to the process of collecting a particular macromolecule or macromolecules from the biological sample. Subsequent to isolating or extracting macromolecule(s) from the sample, they may be further purified by steps well known to those of ordinary skill in the art.

Ways of isolating DNA and RNA from a biological sample can be readily found in laboratory manuals identified above. Furthermore, methods for extracting lipids and carbohydrates are well known to those of skill in the art. See for example, Bucke, 1999; Lindhorst, 2003; Scherz and Bonn, 2002; El Rassi, 1995; Lees and Stanley, 1957; Christie, 1993; Eder et al., 1993; and Manner and Maxwell, 1981.

Furthermore, reagents may be employed for such isolation techniques. Such reagents include, but are not limited to, Totally RNA™, RNAqueous™, RNAwiz™, and RiboPurem™.

E. Preparation of Biological Samples for Assays or Evaluation

Other aspects of the invention concern preparing biological samples for subsequent evaluation or assays. Biological samples can be prepared with compositions of the invention or according to methods of the invention for histological or pathological analysis. Such methods are well known to those of skill in the art, for example, Young and Heath, 2000; Sternberg, 1992; Junqueria et al., 1998. Tissue sections can be made from biological samples prepared according to the invention. Such tissue sections may then be applied to a fixed medium, such as a slide for evaluation.

Sections of biological samples can be prepared according to standard techniques of histology or histochemistry. For example, the sample may first be embedded in a substance known as "embedding agent" that hardens to a firm, easily sectioned material. Commonly employed embedding agents include, but are not limited to paraffin, nitrocellulose, glue, collagen (denatured or non-denatured), fibronectin, laminin, gum syrup, OCT compounds, and various formulations of plastic polymers. The embedding agent is allowed to solidify around and between the sample or samples. For paraffin embedding, dehydration of the sample(s) is generally required prior to embedment to remove excess water or moisture. Typically, dehydration is accomplished by immersing the sample in increasing concentrations of dehydrating agent such as alcohol and the like. Traces of dehydrating agent are then removed by clearing agents immediately before embedment. Most commonly used clearing agents are benzene, chloroform, toluene, xylene, dioxane and mixtures of various oils.

Sectioning of the samples may be implemented using a variety of cutting instruments well known to those of skill in the field. Representative instruments are a standard microtome for cutting sections having a vertical thickness ranging from about 1 to 100 microns, an ultramicrotome for sections thinner than 1 micron, and a cryostat microtome for frozen sections. Protocols for sectioning, dehydration, and/or embedding can be readily revised based on a variety of well-established protocols for histological analyses (see Animal Tissue Techniques, 1967, and protocols posted at http://www.gac.edu/; http://www.ccc.nottingham.ac.uk/; http://www.hei.org/). Also, U.S. Pat. Nos. 5,614,376, 5,843,657, and 6,406,840 are specifically incorporated by reference.

It is contemplated that in some embodiments of the invention, samples are imbedded and then used for extraction of macromolecules, such as demonstrated in U.S. Pat. No. 6,428,963, which is hereby incorporated by reference.

F. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Process for Isolating RNA

Tissues were from Swiss Webster strain mice that had been dissected and quick-frozen in liquid nitrogen by a commercial supplier (Pel-Freeze, Rogers, Ark.). RNA samples were isolated from the indicated tissues after the treatments described using a dual-phenol-chloroform extraction (the Totally RNA™ kit, Ambion, Inc.). After the tissue samples were treated as described, they were dropped directly into homogenization solution (4 M guanidinium thiocyanate (GuSCN)), 25 mM sodium citrate, pH 7.2, 0.5% N-lauroyl sarcosine, 100 mM β-mercaptoethanol) and homogenized with a rotor-stator type homogenizer at high speed for 30 sec. For each experiment, a control sample of frozen tissue was processed similarly by dropping the chunk of frozen tissue directly in the lysis buffer and homogenizing until a uniform consistency was realized. RNA was then extracted from this mixture by using two sequential phenol-chloroform extractions as prescribed for the Totally RNA™ purification protocol (Ambion, Inc.). These samples were concentrated using alcoholic precipitation (procedure described in Sambrook, 2001 and redissolved in water. Alternatively, the raw homogenate was extracted for RNA using the RNAqueous™ kit protocol (Ambion, Inc.). For this procedure, the homogenate is added to an equal volume of 64% ethanol and passed over a glass-fiber filter, which selectively adsorbs the RNA. The RNA is released from the filter with water after several washes.

Example 2

Criteria for Analysis of RNA To Determine if it is "Intact"

Assays on RNA are routinely performed to assess the intactness of such samples. The degree of intactness was used to gauge the quality the RNA recovered from tissues that had been transitioned in the treatment solution and compared to RNA samples isolated directly from frozen tissue.

The RNAs prepared from each sample were analyzed by electrophoretic systems. When RNA degradation occurs, the 28S breaks down faster than the 18S, so that the sharpness of the two rRNA bands and the ratio of 28S to 18S rRNA provides a good estimate of the RNA quality, with moderately degraded samples possessing a 28S band that is unclear or obviously in deficit to the 18S band (personal observations).

The main electrophoretic system employed for analysis was glyoxal-denatured agarose gels (procedure described in Sambrook, 2001). Many of the samples analyzed by this system were also analyzed on a capillary electrophoresis system (Bioanalyzer 2100, Agilent Technologies, Palo Alto Calif.). This second system provided an electrophoretic profile that mirrored the results of the first, while adding the capability to quantify the area under regions of the profile. This enabled the precise measurement of the relative areas of 18S and 28S rRNA peaks. The inventors have found that good RNA preparations have a 28S/18S ratio of 1.0 or greater, although this is variable with the sample source (organ, species of tissue donor, state of animal at sacrifice, etc.).

Example 3

Tissues in Various Solvents

Six solvents selected from the CRC Handbook of Chemistry and Physics were tested for their low melting point and miscibility with water: methanol, ethanol, isopropanol, methoxyethanol, ethyl acetate, and acetic anhydride. This set of solvents are all water-miscible and have melting points below −70° C., they are relatively inexpensive to produce. Also tested was a mixture of ethanol:methanol:isopropanol in a 18:1:1 mixture ("reagent alcohol," cat #6590-1, Ricca Chemical Co., Arlington, Tex.). Mouse livers (from Swiss Webster strain mice, obtained flash-frozen from Pel-Freeze, Rogers, Ak., and maintained at −80° C. for three or more days) were placed directly into an excess of the solvent (greater than 10 volumes) at −20° C. and incubated in the solvent at −20° for 18 hr. After this incubation, the tissues were all rendered to a state resembling leather. The samples were removed from the solvent and placed immediately into a standard homogenization solution and homogenized and extracted as described (Example 1). The RNA extracted was analyzed by both gel and capillary electrophoresis as described in Example 2.

FIGS. 1A-1-FIG. 1A-4 and FIG. 1B-1-FIG. 1B-4 show the capillary electrophoresis scans of RNA extracted from the mouse tissue soaked in the seven organic solvents at −20° C. overnight versus a sample kept frozen and extracted in parallel. Degradation is indicated not only in the diminution of the 28S peak, but in the accrual of material between the two rRNA peaks. Table 1 elaborates on the visual data, by providing a ratio of the peaks' areas. It shows the effect of soaking frozen mouse liver in various organic solvents (−20° C., 18 hr) prior to extraction on rRNA ratios of extracted RNA. Of the solvents tested, the alcohols uniformly generated the highest 28S:18S ratios (1.31-1.39). These surpass the quality obtained from frozen tissue directly processed into lysis solution (ratio of 0.89) as well.

TABLE 1

| soaking solvent | 28S/18S ratio |
| --- | --- |
| none (frozen) | 0.89 |
| Ethyl Acetate | 0.79 |
| Acetic Anhydride | 1.00 |
| Methoxyethanol | 1.24 |
| Isopropanol | 1.31 |
| Methanol | 1.37 |
| Ethanol | 1.39 |
| reagent alcohol | 1.39 |

Example 4

Brain Tissue in EtOH, with or without DMSO

Figure 2A:
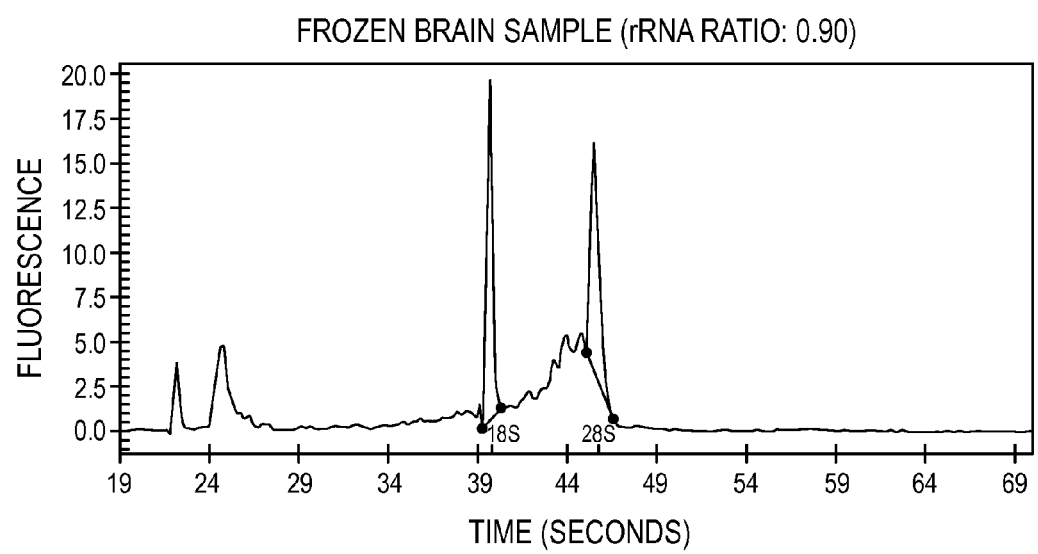
FIG. 2A-FIG. 2C. Capillary electrophoresis scans of RNA extracted from frozen brains of mice that had been soaked in ethanol, with or without DMSO.
Figure 2B:
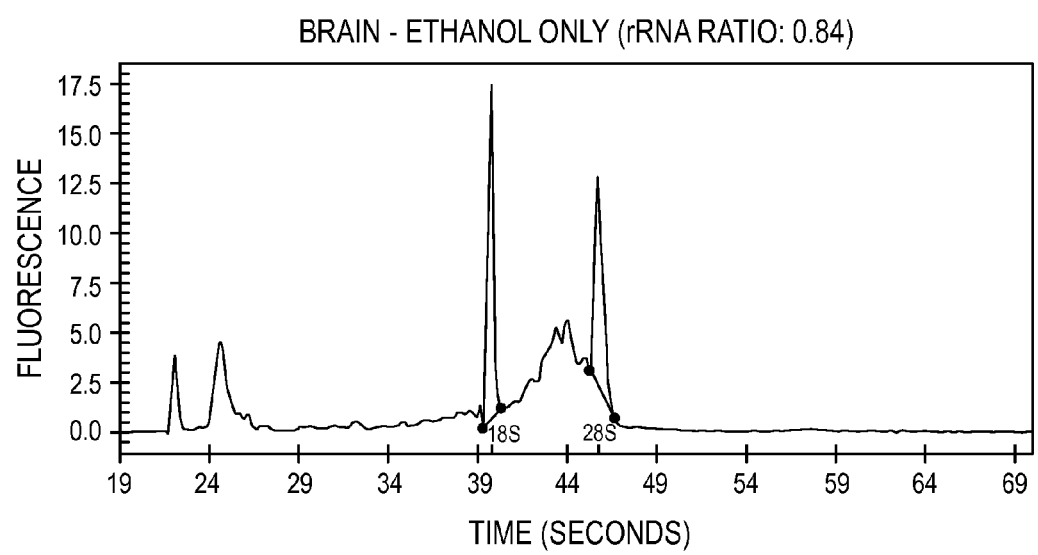
Figure 2C:
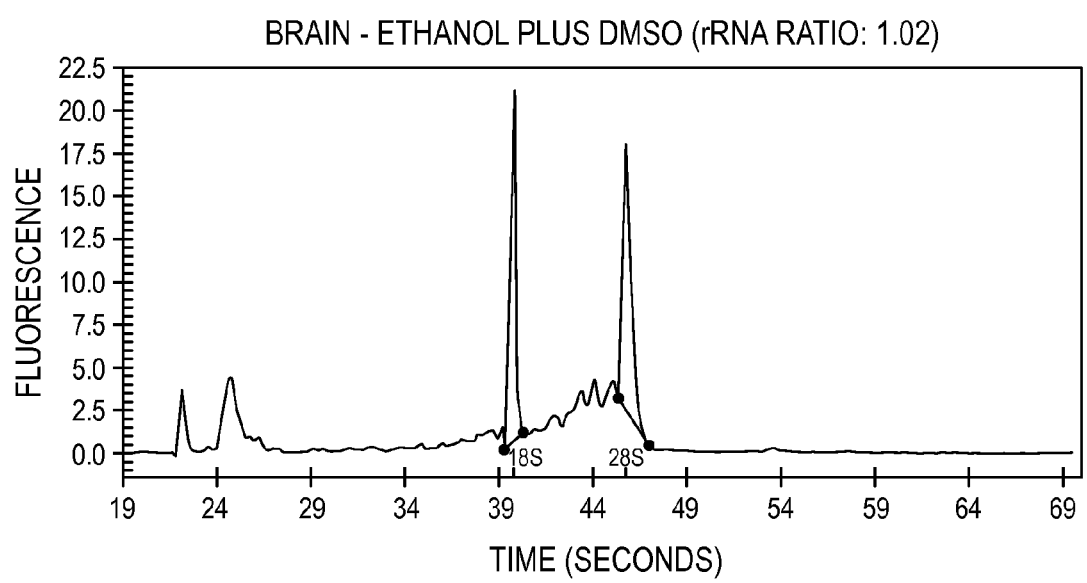

Frozen mouse brains (from Swiss Webster strain mice, obtained flash-frozen from Pel-Freeze, Rogers, Ak., and maintained at −80° C. for three or more days) were either soaked overnight in absolute ethanol or absolute ethanol plus 5% DMSO (cat #27,043-1, Aldrich Chemical Co, Milwaukee, Wis.), or processed directly for RNA. The soak was performed for 10 hr at −20° C. FIG. 2A-FIG. 2C show the effect of including 5% DMSO in an ethanol transfer soak. The samples from the ethanol-only-soaked brain show a greater amount of material between the two rRNA peaks as well as a lower 28S:18S ratio than the sample soaked in ethanol plus DMSO, indicating the addition of DMSO reduced the level of degradation of the RNA.

Example 5

Kidney tissue in EtOH, with or without DMSO

Frozen mouse kidney tissues were incubated in ethanol with 0, 0.1, 0.5, 1, 2, 4, 8, 12, and 20% DMSO at −20° for 18 hr, then processed using Ambion's Totally RNA@™ protocol. Inclusion of at least 1% DMSO appeared to aid RNA protection, as the samples with 1% or more DMSO had stronger 28S bands on an agarose gel than the sample processed directly from frozen tissue or those soaked in ethanol only.

Example 6

Tissues in Solvent with Protein Modification Additives

Since the activity of RNase A-type nucleases utilizes 2 histidines at its active site, the inclusion of small molecules known to form covalent adducts, especially on histidine, could potentially permanently inactivate a large percentage of the nucleolytic activity. Such inactivation may occur on rehydration at the homogenization step. To test this, several known protein-modification agents were included separately with the alcohols from Example 2 to determine if there were any additional benefit. The compounds chosen were acetylsalicylic acid, 2-bromoacetamide, iodoacetamide, adipoyl chloride, iodoacetic acid, 2-chloroacetamide, adipic dihydrazide, cyanuric acid, acetic anhydride, 1,4-butanediol, and sebacoyl chloride. All were dissolved in the solvent at concentrations of 0, 1, and 5% for the test. After soaking mouse liver at −20° C. for 20 hr with each of these additives, samples were processed using the Totally RNA™ protocol. Of these, RNA intactness was greater when acetylsalicylic acid, 2-bromoacetamide, and iodoacetamide was added at 1%, as determined by the appearance of rRNA bands on an ethidium-stained agarose gel. The effect was not noticeably increased at the higher concentration for any.

Example 7

Frozen Tissues from Several Sources

Mouse liver, heart, pancreas, kidney, brain were tested for effectiveness of the soaking procedure, performing an overnight soak in ethanol plus 5% DMSO at −20° C. All tissues showed a beneficial effect from the soaking, both in terms of handling of the tissue and the intactness of the RNA as observed on using agarose gel electrophoresis.

Example 8

Stability of Soak Solution at −20° C.

Mouse liver tissue that had been soaked in ethanol at −20° C. for several months (up to a year) were extracted for RNA using the RNAqueous™ protocol. No degradation was seen by agarose gel electrophoresis.

Example 9

Stability in Soak Solution at Ambient Temperature

Frozen mouse kidney and pancreas tissues were soaked in absolute ethanol and reagent alcohol, each with 5% DMSO, on (wet) ice for 10, 20, 30, 40, and 50 min. Samples were isolated using the Totally RNA™ protocol and examined on an agarose gel as described. The intactness of the RNA appeared unaffected. This provides some relief from the time constraints of frozen tissue, which must be processed immediately upon immersion in homogenization solution.

Example 10

Volume of Soakings with or without Iodoacetamide

Frozen mouse kidney halves were soaked in absolute ethanol with 5% DMSO and 2 mM glacial acetic acid, in volumes of 0.5, 1, 2, 5, and 10× the volume of the tissue sample. This series was done in parallel with a second series that also contained 2% iodoacetamide. Each sample was extracted for RNA using die Totally RNA™ protocol and the RNA preparations were examined on an ethidium-stained agarose gel. The iodoacetamide provided a protectant action such that one volume of the soak with iodoacetamide soak protected the RNA as well as 5 volumes of the soak without iodoacetamide.

Example 11

Soaking with Various Concentrations of Alcohol

Two sets of five frozen liver samples were soaked in 50-90% alcohol (in 10% increments), with 1% and 5% DMSO (time of soak 24 hr). RNA was extracted from all samples after removal from the "soak" solution and exposure to ambient temperature for 30 minutes, using the Totally RNA™ protocol. Equal amounts of all samples were run on a denaturing (glyoxal) agarose gel. Those samples permeated in 60% alcohol and lower with 1% DMSO generated degraded RNA as evidenced by a low molecular weight smear. The samples permeated in the various alcohol, concentrations plus 5% DMSO were markedly more stable, where the 18S rRNA band was visible in the 50% alcohol sample and the RNA profile looked normal for the 60% alcohol sample.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.
U.S. Pat. No. 6,204,375
U.S. Pat. No. 5,256,571
U.S. Pat. No. 5,614,376
U.S. Pat. No. 5,843,657
U.S. Pat. No. 6,406,840
Animal Tissue Techniques, Humason (Eds.), Freeman and Company, 1967.
Ausubel et al., In: Current Protocols in Molecular Biology, John, Wiley and Sons, Inc, NY, 1994.
Bucke, In: Carbohydrate biotechnology protocols, Methods in Biotechnology, (10), Humana Press, 1999.
Christie, In: Advances in lipid methodology, Oily Press, Dundee, 195-213, 1993.
Eder et al., Clin. Chim. Acta., 219(1-2):93-104, 1993.
El Rassi, In: Carbohydrate analysis: High performance liquid chromatography, and capillary electroporesis, Oklahoma State Univ., Elsevier Science, Stillwater, Okla., 1995.
Esser et al., Cytometry, 121 (4):382-386, 1995.
Folch et al., J. Biological Clem., 226:497-509, 1957.
Fukatsu, Mol. Ecol., 8(11):1935-1945, 1999.
Hara and Radin, Anal. Biochem., 90(1):420-426, 1978.
Harlow and Lane, Antibodies: A Laboratory manual, Cold Spring Harbor Laboratory, 1988.
Junqueria et al., In: Basis histology, McGraw-Hill/Appleton and Lange,; ISBN 0838505902, 9$^{th}$ Ed., 1998.
Lindhorts, In: Essentials of carbohydrate chemistry and biochemistry, John Wiley and Sons, Inc., NY, 2003.
Marmer and Maxwell, Lipids, 16(5):365-371, 1981.
Rapley and Manning, In: RNA Isolation and Characterization Protocols, Humana Press, Inc. Totowa, N.J., 1998.
Safneck et al., Acta Cytol., 45(3):365-371, 2001.
Sambrook et al., In: Molecular cloninig, Cold Spring Harbor Laboratory Press, Cold Spring Harbor, N.Y., 2001.
Scherz and Bonn, In: Analytical chemistry of carbohydrates, John Wiley and Sons, NY, 2002.
Sternberg, In: Histology for pathologists, Raven Press, NY-1992.
Young and Heath, In: Wheater's functional histology, Churchill Livingstone, ISBN: 0443056129, 3$^{rd}$ and 4$^{th}$ Ed., 2000.

What is claimed is:

1. A kit for extracting a macromolecule from a biological sample comprising, in a suitable container, a soak solution that is
    i) at least 60% comprised of one or more water-miscible solvents having a melting temperature below about 0° C. wherein one of the one or more water-miscible solvents is ethanol,
    ii) at least 1% and up to 20% comprised of DMSO and
    iii) has a pH of about 5-6.
2. The kit of claim 1, wherein the soak solution is at least 60% comprised of one or more water-miscible solvents having a melting temperature below about −20° C.

3. The kit of claim 1, wherein the soak solution is at least 90% comprised of one or more water-miscible solvents having a melting temperature below about −20° C.

4. The kit of claim 1, wherein the one or more water-miscible solvents have a melting temperature below −50° C.

5. The kit of claim 1, wherein the one or more water-miscible solvents have a melting temperature below −70° C.

6. The kit of claim 1, wherein the one or more water-miscible solvents have a melting temperature below −100° C.

7. The kit of claim 2, wherein one or more of the water miscible solvents is an alcohol.

8. The kit of claim 7, wherein the soak solution comprises ethanol, methanol, and isopropanol.

9. The kit of claim 1, further comprising a homogenization solution.

10. The kit of claim 9, wherein the homogenization solution comprises a protein denaturant.

11. The kit of claim 10 wherein the protein denaturant comprises guanidinium.

12. The kit of claim 2, wherein the soak solution is at least 70% comprised of one or more water-miscible solvents.

13. The kit of claim 12, wherein the soak solution is at least 80% comprised of one or more water-miscible solvents.

14. The kit of claim 1, wherein the soak solution contains at least two water-miscible solvents.

15. The kit of claim 14, wherein the soak solution contains at least three water-miscible solvents.

16. The kit of claim 15, wherein the soak solution contains at least four water-miscible solvents.

17. A kit for extracting a macromolecule from a biological sample comprising, in a suitable container: a soak solution that is i) at least about 90% ethanol, ii) about 4%-5% comprised of DMSO and iii) has a pH of about 5.

18. A kit for extracting a macromolecule from a biological sample comprising, in a suitable container: a soak solution that is about 89%-90% ethanol, about 4%-5% comprised of DMSO, 4%-5% of a combination of methanol and isopropanol, and has a pH of about 5.

* * * * *